United States Patent [19]

Sato et al.

[11] Patent Number: 4,705,863

[45] Date of Patent: Nov. 10, 1987

[54] PROCESS FOR PRODUCING PYRAZOLO[1,5-B][1,2,4]TRIAZOLE DERIVATIVES

[75] Inventors: Tadahisa Sato; Toshio Kawagishi; Nobuo Furutachi, all of Minami-ashigara, Japan

[73] Assignee: Fuji Photo Film Co., Ltd., Kanagawa, Japan

[21] Appl. No.: 713,989

[22] Filed: Mar. 20, 1985

[30] Foreign Application Priority Data

Mar. 22, 1984 [JP] Japan ................................. 59-53443

[51] Int. Cl.$^4$ .......................................... C07D 487/04
[52] U.S. Cl. .................................... 548/262; 548/362
[58] Field of Search ............................... 548/262, 362

[56] References Cited

U.S. PATENT DOCUMENTS

| | | | |
|---|---|---|---|
| 3,725,067 | 3/1973 | Bailey et al. | 96/56.5 |
| 4,540,654 | 9/1985 | Sato et al. | 430/381 |
| 4,621,046 | 11/1986 | Sato et al. | 430/381 |

Primary Examiner—Richard L. Raymond
Attorney, Agent, or Firm—Birch, Stewart, Kolasch and Birch

[57] ABSTRACT

Pyrazolo[1,5-b][1,2,4]triazole derivatives are produced by ring closure of an amidoxime compound having a pyrazolyl group. The product can be used as a photographic magenta coupler as such. It is also useful as an intermediate for the magenta coupler, as a dye developer for diffusion transfer process, as an intermediate for the dye releasing agent, and as an intermediate for the photographic sensitizing dye.

14 Claims, No Drawings

PROCESS FOR PRODUCING PYRAZOLO[1,5-B][1,2,4]TRIAZOLE DERIVATIVES

BACKGROUND OF THE INVENTION

1. Field of the Invention

The present invention relates to a process for producing novel pyrazolo[1,5-b][1,2,4]triazole derivatives.

2. Description of the Prior Art

A 5-5 condensed polycyclic compound represented by general formula (I) depicted below is named "azapentalene"

(I)

wherein,
broken lines (— — — —) indicate three double bonds that shift from one position to another,
dots (•), located at the apices, each indicate a nitrogen atom or carbon atom.

In addition to the nitrogen atom at the bridgehead position, the compound has at least one more nitrogen atom and therefore it has 2 to 6 nitrogen atoms in total, and the interaction of 10 π-electrons (including the lone pair of electrons in the nitrogen atom at the bridgehead position and those in other nitrogen atom(s) if present is possible in the molecule. This compound aroused researchers' interest from viewpoints of structural chemistry, physiological activity and applications as a photographic magenta coupler. (See J. Elgureo, R. Jacquier, S. Mignonac-Mondon, *J. Heterocyclic. Chem.*, 10, 411 (1973); H. Koga, M. Hirobe, T. Okamoto, *Chem. Pharm. Bull.*, 22, 482 (1974); J. Bailey, *J. C. S. Perkin I* 2047 (1977); Japanese Patent Publication No. 27411/1972; and Japanese Patent Laid-open No. 129586/1975.)

However, the conventional azapentalene compound a pyrazolo[5,1-c][1,2,4]triazole as a photographic magenta coupler are not necessarily satisfactory in hue and fastness to light and heat.

In order to develop a new coupler compound which is free of the disadvantages of the conventional azapentalene compound, the present inventors carried out a series of researches which have led to the finding that an azapentalene compound having a new skeleton is synthesized by ring closure of an amidoxime compound having a pyrazolyl group and that this azapentalene compound is satisfactory to achieve the above-mentioned objective. This compound is a pyrazolo[1,5-b][1,2,4]triazole derivative, which is disclosed in the copending continuation-in-part of application Ser. No. 702,691, Ser. No. 590,818, now U.S. Pat. No. 4,540,654.

SUMMARY OF THE INVENTION

Accordingly, this invention provide a process for producing pyrazolo[1,5-b][1,2,4]triazole derivatives by ring closure of an amidoxime compound.

It is the first object of this invention to provide a process for synthesizing an azapentalene compound having a new skeleton.

It is the second object of this invention to provide a process for producing pyrazolo[1,5-b][1,2,4]triazole derivatives, azapentalene compounds, from an amidoxime compound having a pyrazolyl group.

It is the third object of this invention to provide a process for producing pyrazolo[1,5-b][1,2,4]triazole derivatives, new azapentalene compounds, useful as a magenta coupler for color photography or an intermediate thereof, as a dye developer for color diffusion transfer process, as an intermediate for synthesis of the dye releasing agent, and as an intermediate for the production of a photographic sensitizing dye.

It is the fourth object of this invention to provide a process for producing pyrazolo[1,5-b][1,2,4]triazole derivatives useful for other uses such as intermediates for the production of physiologically active substances or pharmaceutical products.

Other and further objects, features, and advantages of the invention will appear more fully from the following description.

DETAILED DESCRIPTION OF THE INVENTION

According to this invention, there is provided a process for producing pyrazolo[1,5-b][1,2,4]triazole derivatives which comprises subjecting a compound represented by the formula:

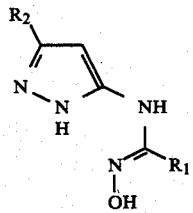
(II)

(where $R_1$ and $R_2$ each denote a hydrogen atom or substituted or unsubstituted alkyl or aryl group)
to ring closure to give a compound represented by the formula:

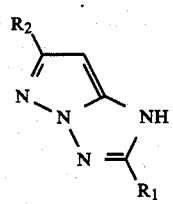
(III)

(where $R_1$ and $R_2$ are defined as above).

The compound of the above formula (II) used in this process is prepared by reacting aminopyrazole represented by the formula:

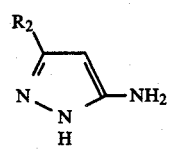
(IV)

(where $R_2$ is defined as above)
with ortho ester represented by the formula:

$$R_1C(OR_3)_3 \qquad (V)$$

(where $R_1$ is defined as above and $R_3$ denotes an alkyl group)

or ketene acetal represented by the formula:

$$R_{1a}CH=C(OR_3)_2 \qquad (V')$$

(where $R_{1a}$ is a group which, in combination with —CH$_2$—, forms the substituted or unsubstituted alkyl group of the above-mentioned $R_1$ group; and $R_3$ is defined as above)
to give an imido ester of pyrazole represented by the formula:

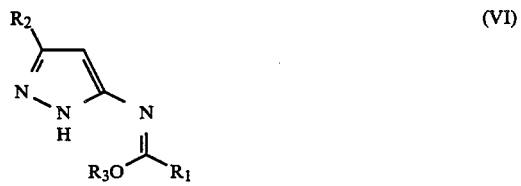

(VI)

(where $R_1$, $R_2$, and $R_3$ are defined as above) and subsequently reacting the imido ester of pyrazole with hydroxylamine.

From the compound of formula (III) obtained by the above-mentioned process a compound represented by the formula:

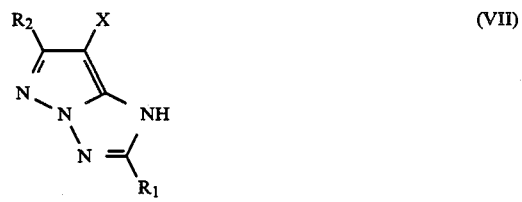

(VII)

(where $R_1$ and $R_2$ are defined as above; and X denotes a coupling split-off group)
can be prepared upon introduction of a coupling split-off group.

Examples of the alkyl groups in the substituent $R_1$, $R_2$, and $R_3$ of the above formulas (II), (III), (IV), (V), (V'), (VI), and (VII) range from lower alkyl groups such as methyl, ethyl, propyl, and butyl groups to higher alkyl groups (containing up to 22 carbon atoms) such as pentyl, hexyl, heptyl, octyl, decyl, undecyl, tridecyl, and octadecyl groups. An alkyl group may be a straight or branched chain.

The aryl group in the substituent $R_1$ and $R_2$ includes a phenyl group and a naphthyl group. As the substituted alkyl group, $R_1$ and $R_2$ include halogen-substituted alkyl groups, e.g., a 2-chloroethyl group and a trifluoromethyl group; alkoxy-substituted alkyl groups, e.g., a 2-ethoxytridecyl group; acylamido-substituted alkyl group, e.g., a 2-acetomidoethyl group; sulfonamido-substituted alkyl group, e.g., a 2-methanesulfonamidoethyl group; and alkyl groups substituted by a substituted or unsubstituted aryl group, e.g., a 3-(2,4-di-t-amylphenoxy)propyl group, a 3-(4-(2-(4-(4-hydroxyphenylsulfonyl)phenoxy)dodecaneamido)phenyl)propyl group, benzyl group, and phenetyl group. As the substituted aryl group $R_1$ and $R_2$ include a halogenophenyl group, a nitrophenyl group, a cyanophenyl group, and an alkoxyphenyl group. In addition, the groups represented by $R_1$ and $R_2$ may have a substituent group such as alkoxyl group, nitro group, and halogen atom which are inactive to the reaction.

In the case where $R_1$ or $R_2$ in the pyrazolo[1.5-b][1,2,4]triazole derivative has a substituent group as mentioned above, the desired compound can be prepared according to the process scheme illustrated below directly. Alternatively, the desired compound may be produced by first preparing the basic skeleton of the pyrazolo[1,5-b][1,2,4]triazole ring, and then introducing a desired substituent group in the subsequent reactions. For example, as demonstrated in Example 4 mentioned later the amino group in compound 20 can be converted into the acid anilide in compound 22 by the known method.

The process of this invention may be illustrated by the following process scheme.

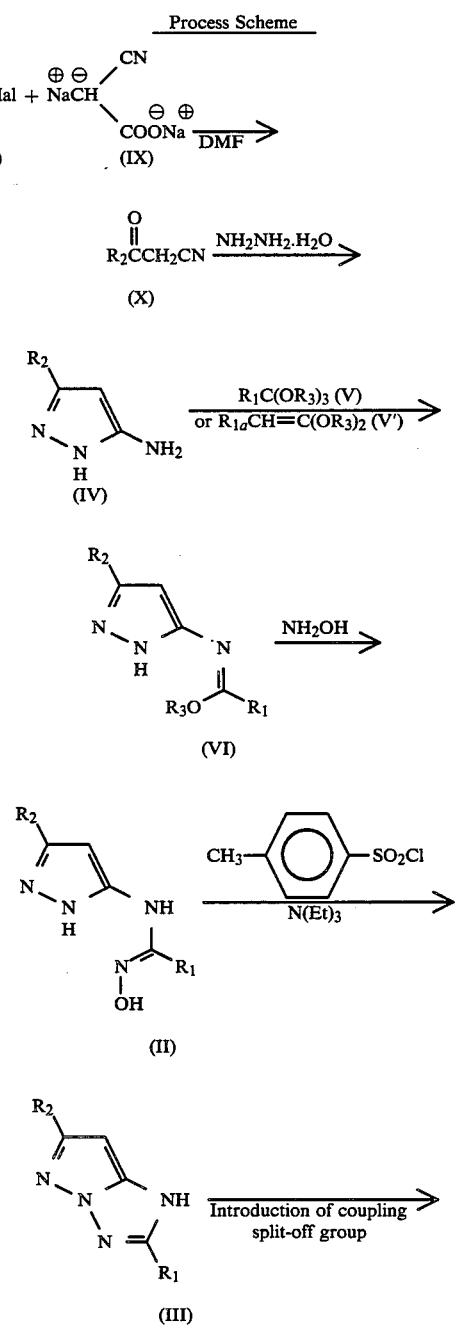

-continued
Process Scheme

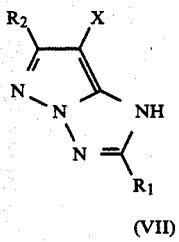

(VII)

(where Hal denotes a halogen atom.)

The preferred embodiment of this invention is described with reference to the process scheme shown above.

The reaction of aminopyrazole (IV) with orthoester (V) or ketene acetal (V') is conducted preferably in a solvent at 40° to 150° C., preferably 100° to 120° C., for 10 minutes to 20 hours. If the reaction temperature is lower than the above-mentioned lower limit, the reaction takes a longer time to complete. If the reaction temperature is higher than the upper limit, the yield might decrease in some cases. Examples of the suitable solvent include aromatic hydrocarbons, e.g., benzene, toluene, and xylene; halogenated hydrocarbons, e.g., chloroform, dichloroethane, and trichloroethane; and ethers, e.g., tetrahydrofuran and dioxane. In the case of the reaction with ketone acetal, an acid catalyst should be used without fail; and in the case where the reaction with orthoester is slow, an acid catalyst should preferably be used. Examples of the acid catalyst include methanesulfonic acid, p-toluenesulfonic acid, and trifluoroacetic acid.

The molar ratio of aminopyrazole (IV) to orthoester (V) should preferably be in the range of 2:1 to 1:2.

Examples of aminopyrazole (IV) include 3-aminopyrazole, 5-amino-3-methylpyrazole, 5-amino-3-phenylpyrazole, and 5-amino-3-[3'-(p-nitrophenyl)-propyl]pyrazole. Examples of orthoester (V) include triethyl orthoformate, triethyl orthoacetate, triethyl orthopropionate, triethyl orthobutyrate, trimethyl orthoisocaproate, and trimethyl ortho-4-(p-nitrophenyl)-butyrate. Examples of ketene acetal (V') include methylketene diethylacetal, phenylketene dimethylacetal, and p-nitrophenylketene dimethylacetal.

Commercially available aminopyrazole (IV) may be used; but when necessary it can be synthesized by first reacting an acid halide (VIII) with an enolate of sodium cyanacetate (IX) to give an oxopropiononitrile derivative (X) and then reacting the derivative (X) with hydrazine. In the case where $R_2$ is a methyl group, (IV) (wherein $R_2$=—$CH_3$) can be synthesized by reacting 3-aminocrotononitrile, which is readily synthesized from acetonitrile and sodium, with hydrazine (J. Heterocycl. Chem., Vol. 11, p 423, 1974).

Then, an imido ester compound of formula (VI) is reacted with hydroxylamine to give an amidoxime compound of formula (II). This reaction may be conducted at temperature from 0° to 80° C. for 0.5 to 12 hours. If the reaction temperature is lower than the above-mentioned lower limit, the reaction may not proceed sufficiently, while if it is higher than the upper limit, the decomposition of hydroxylamine might occur, and side reactions will take place in case an excess amount of hydroxylamine is used. Preferable reaction solvent is an alcohol such as methanol and ethanol. In this reaction, the preferred molar ratio of hydroxylamine to the imido ester is 1 to 20.

A pyrazolotriazole compound of formula (III) is prepared from the amidoxime compound of formula (II) obtained by the above-mentioned reaction by ring closure. This reaction can be conducted using a proper dehydrating agent in the presence of a base. This reaction should preferably be performed in an inert solvent such as tetrahydrofuran and dioxane using a dehydrating agent in an amount necessary (usually one equivalent) to permit the reaction to proceed sufficiently. The preferred temperature is 40° to 100° C. and the preferred reaction time is 2 to 10 hours. Examples of the dehydrating agent include p-toluenesulfonyl chloride, methanesulfonyl chloride, trifluoromethanesulfonyl chloride, phosphorus oxychloride, and thionyl chloride. Examples of the base include tertiary amines such as triethylamine and diisopropylethylamine, pyridine, and 4-dimethylaminopyridine. The amount of the base may be 0.5 to 2 equivalent, and preferably 1 equivalent.

In the above-mentioned process scheme, the intermediate compounds may be used, without isolation, for the subsequent reactions but usually they are isolated and purified by a proper means such as solvent extraction, recrystallization, column chromatography, and thin layer chromatography.

According to the process of this invention, the pyrazolo[1,5-b][1,2,4]triazole compound represented by the formula (III) may be further treated to introduce a coupling split-off group known for a photographic coupler into the 7-position. The method to introduce a coupling split-off group is known in the production of photographic coupler in order to reduce the quantity of silver halide and to adjust the rate of coupling rection with the oxidation product of an aromatic primary amine resulting from oxidation by silver halide.

In what follows, we will explain the general method of introducing the coupling split-off group.

(1) Method to connect an oxygen-atom

It is possible to synthesize 7-hydroxypyrazolo[1,5-b]triazole by reacting the 4-equivalent coupler synthesized according to the process of this invention, a pyrazolo[1,5-b]triazole type coupler, and the oxidation product of an aromatic primary amine with one another to form a dye, and subsequently hydrolyzing the dye in the presence of an acid catalyst to obtain a ketone, and finally hydrogenizing the ketone using a Pd-carbon catalyst or subjecting the ketone to reduction treatment with Zn-acetic acid or sodium borohydride. The thus prepared 7-hydroxypyrazolo[1,5-b]triazole is reacted with a halide to give a desired coupler in which an oxygen atom is connected. (See U.S. Pat. No. 3,926,631 and Japanese Patent Application (OPI) No. 70817/1982.)

(2) Method to connect a nitrogen atom

There are three major methods of connecting a nitrogen atom. According to the first method (as disclosed in U.S. Pat. No. 3,419,391), the coupling active site is nitrosized by a proper nitrosizing agent and the nitroso group is subjected to reduction by a proper method (e.g., hydrogenation using a Pd-carbon catalyst and chemical reduction with stannous chloride) to give 7-aminopyrazolo[1,5-b]triazole, and this product is reacted with a halide to give an amide compound.

According to a second method (as disclosed in U.S. Pat. No. 3,725,067), the 7-position is halogenated with a proper halogenating agent such as sulfuryl chloride, chlorine gas, bromine, N-chlorosuccinimide, and N-bromosuccinimide, and subsequently the nitrogen hetero ring is introduced in the presence of a proper base catalyst, triethylamine, sodium hydroxide, azabicyclo[2,2,2]octane, or anhydrous potassium carbonate, whereby it is possible to prepare a coupler in which a nitrogen atom connects to the 7-position. This method can be applied to the synthesis of a compound having a phenoxy group at the 7-position among the compounds having the connection by an oxygen atom.

A third method is effective in introducing a 6π or 10π electron aromatic nitrogen hetero ring into the 7-position. According to this method, as disclosed in Japanese Patent Publication No. 36577/1982, 2 or more moles of 6π or 10π electron aromatic nitrogen hetero ring is added to per 1 mol of the 7-halogen derivative synthesized according to the above-mentioned second method, followed by heating to 50°–150° C. without solvent or by heating at 30° to 150° C. in a non-protonic polar solvent such as dimethyl formamide, sulfolane, and hexamethylphosphotriamide. Thus it is possible to introduce an aromatic nitrogen hetero ring connected by a nitrogen atom at the 7-position.

(3) Method to connect a sulfur atom

A coupler with an aromatic mercapto group or hetero ring mercapto group substituted at the 7-position can be synthesized according to the method disclosed in U.S. Pat. No. 3,227,554. That is, aryl mercaptan, hetero ring mercaptan, and its corresponding disulfide are dissolved in a halogenated hydrocarbon solvent; chlorine or sulfuryl chloride is added to form sulfenyl chloride; and the sulfenyl chloride is added to 4-equivalent pyrazolo[1,5-b]triazole coupler dissolved in a non-protonic solvent. The introduction of an alkylmercapto group into the 7-position can be accomplished according to the method disclosed in U.S. Pat. No. 4,264,723. That is, a mercapto group is introduced into the coupling active site of a coupler and the mercapto group is reacted with a halide; or the synthesis is achieved in one step by using S-(alkylthio)isothiourea hydrochloride (or hydrobromide).

According to the process of this invention, the substituent groups $R_1$ and $R_2$ at the 2- and 6-position of pyrazolo[1,5-b][1,2,4]triazole compound represented by the formula (III) may be replaced with photochemically acceptable desired radicals by employing the known method such as the above-mentioned method for the introduction of a coupling split-off group.

The pyrazolo[1,5-b][1,2,4]triazole derivative which is formed utilizing the process of this invention is represented by the formula (XI) below.

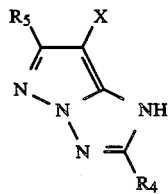

(XI)

(where $R_4$ and $R_5$ each denote a hydrogen atom or substituent group; and X denotes a hydrogen atom or coupling split-off group).

$R_4$ and $R_5$ each are preferably a hydrogen atom, halogen atom, aliphatic group, aryl group, heterocyclic group, cyano group, alkoxy group, aryloxy group, acylamine group, anilino group, ureido group, sulfamoylamino group, alkylthio group, arylthio group, alkoxycarbonylamino group, sulfonamido group, carbamoyl group, sulfamoyl group, sulfonyl group, alkoxycarbonyl group, heterocyclic oxy group, acyloxy group, carbamoyloxy group, silyloxy group, aryloxycarbonylamino group, imido group, heterocyclic thio group, sulfinyl group, aryloxycarbonyl group, and acyl group. X denotes a hydrogen atom, halogen atom, or carboxyl group, or a group that is connected to the carbon at the coupling position through an oxygen atom, nitrogen atom, carbon atom, or sulfur atom. This group is eliminated upon coupling. $R_4$, $R_5$ or X may be divalent to form a bis compound.

In the case where the moiety represented by the formula (XI) is contained in vinyl monomer, ether $R_4$ or $R_5$ denotes a mere connecting group, and the moiety represented by the formula (XI) is connected to the vinyl group through it.

To be more specific, $R_4$ and $R_5$ each denote any one of the following atoms or groups. Hydrogen atom and halogen atom (e.g., chlorine atom and bromine atom). Aliphatic groups ($C_{1-32}$ straight chain or branched chain alkyl group, aralkyl group, alkenyl group, alkynyl group, cycloalkyl group, and cycloalkenyl group, which may have a substituent group connected by an oxygen atom, nitrogen atom, sulfur atom, or carbonyl group, or may be substituted with a hydroxyl group, amino group, nitro group, carboxyl group, cyano group, or halogen atom. Examples of the aliphatic group include methyl group, propyl group, t-butyl group, tridecyl group, 2-methanesulfonylethyl group, 3-(3-pentadecylphenoxy)propyl group, 3-(4-(2-(4-(4-hydroxyphenylsulfonyl)phenoxy)dodecaneamino)-phenyl)propyl group, 2-ethoxytridecyl group, trifluoromethyl group, cyclopentyl group, and 3-(2,4-di-t-amylphenoxy)propyl group.) Aryl group (e.g., phenyl group, 4-t-butylphenyl group), 2,4-di-t-amylphenyl group, and 4-tetradecaneamido phenyl group). Heterocyclic group (e.g., 2-furyl group, 2-thienyl group, 2-pyrimidyl group, and 2-benzothiazolyl group). Cyano group. Alkoxyl group (e.g., methoxy group, ethoxy group, 2-methoxyethoxy group, 2-dodecylethoxy group, and 2-methanesulfonylethoxy group). Aryloxy group (e.g., phenoxy group, 2-methylphenoxy group, and 4-t-butylphenoxy group). Acylamino group (e.g., acetamido group, benzamido group, tetradecaneamido group, α-(2,4-di-t-amylphenoxy)butylamido group, γ-(3-t-butyl-4-hydroxyphenoxy)butylamido group, and α-(4-(4-hydroxyphenylsulfonyl)phenoxy)decane amido group). Anilino group (e.g., phenylamino group, 2-chloroanilino group, 2-chloro-5-tetradecaneaminoanilino group, 2-chloro-5-dodecyloxycarbonylanilino group, N-acetylanilino group, and 2-chloro-5-(α-(3-t-butyl-4-hydroxyphenoxy)-dodecaneamido)anilino group). Ureido group (e.g., phenylureido group, methylureido group, and N,N-dibutylureido group). Sulfamoylamino group (e.g., N,N-dipropylsulfamoylamino group, and N-methyl-N-decylsulfamoylamino group). Alkylthio group (e.g., methylthio group, octylthio group, tetradecylthio group, 2-phenoxyethylthio group, 3-phenoxypropylthio group, and 3-(4-t-butylphenoxy)propylthio group). Arylthio group (e.g., phenylthio group, 2-butoxy-5-t-octylphenylthio group, 3-pentadecylphenylthio group, 2-carboxyphenylthio group, and 4-tetradecaneamidophenylthio group). Alkoxycarbonylamino group (e.g., methoxycarbonylamino group and tetradecyloxycarbonylamino group). Sulfonamido group (e.g., methanesulfonamido group, hexadecanesulfonamido group, benzenesulfonamido group, p-toluenesulfonamido group, octadecanesulfonamido group, and 2-methyloxy-5-butylbenzenesulfonamido group). Carbamoyl group (e.g., N-ethylcarbamoyl group, N,N-dibutylcarbamoyl group, N-(2-dodecyloxyethyl)carbamoyl group, N-methyl-N-dodecylcarbamoyl group, and N-(3-(2,4-di-t-amylphenoxy)propyl)carbamoyl group). Sulfamoyl group (e.g., N-ethylsulfamoyl group, N,N-dipropylsulfamoyl group, N-2-dodecyloxyethyl)sulfamoyl group, N-ethyl-N-dodecylsulfamoyl group, and N,N-diethylsulfamoyl group). Sulfonyl group (e.g., methanesulfonyl group, octanesulfonyl group, benzenesulfonyl group, and toluenesulfonyl group). Alkoxycarbonyl group (e.g., methoxycarbonyl group, butyloxycarbonyl group, dodecyloxycarbonyl group, and octadecyloxycarbonyl group). Heterocyclic oxy group (e.g., 1-phenyltetrazole-5-oxy group and 2-tetrahydropiranyloxy group). Acyloxy group (e.g., acetoxy group). Carbamoyloxy group (e.g., N-methylcarbamoyloxy group and N-phenylcarbamoyloxy group). Silyloxy group (e.g., trimethylsilyloxy group and dibutylmethylsilyloxy group). Aryloxycarbonylamino group (e.g., phenoxycarbonylamino group). Imido group (e.g., N-succinimido group, N-phthalimido group, and 3-octadecenylsuccinimido group). Heterocyclic thio group (e.g., 2-benzothiazolylthio group, 2,4-diphenoxy-1,3,5-triazole-6-thio group, and 2-pyridylthio group). Sulfinyl group (e.g., dodecanesulfinyl group, 3-pentadecylphenylsulfinyl group, and 3-phenoxypropylsulfinyl group). Phosphonyl group (e.g., phenoxyphosphonyl group, octyloxyphosphonyl group, and phenylphosphonyl group). Aryl oxycarbonyl group (e.g., phenoxycarbonyl group). Acyl group (e.g., acetyl group, 3-phenylpropanoyl group, benzoyl group, and 4-dodecyloxybenzoyl group).

X denotes a hydrogen atom, a halogen atom (e.g., chlorine atom, bromine atom, and iodine atom), a carboxyl group or a group connected by an oxygen atom (e.g., acetoxy group, propanoyloxy group, benzoyloxy group, 2,4-dichlorobenzoyloxy group, ethoxyoxazoloyloxy group, pyruvinyloxy group, cinnamoyloxy group, phenoxy group, 4-cyanophenoxyl group, 4-methanesulfonamidophenoxy group, 4-methanesulfonylphenoxy group, α-naphthoxy group, 3-pentadecylphenoxy group, benzyloxycarbonyloxy group, ethoxy group, 2-cyanoethoxy group, benzyloxy group, 2-phenetyloxy group, 2-phenoxyethoxy group, 5-phenyltetrazolyloxy group, and 2-benzothiazolyloxy group), a group connected by a nitrogen atom (e.g., benzenesulfonamido group, N-ethyltoluenesulfonamido group, heptafluorobutanamido group, 2,3,4,5,6-pentafluorobenzamido group, octanesulfonamido group, p-cyanophenylureido group, N,N-diethylsulfamoylamino group, 1-pyperidyl group, 5,5-dimethyl-2,4-dioxo-3-oxazolidinyl group, 1-benzylethoxy-3-hydantoinyl group, 2N-1,1-dioxo-3-(2H)-oxo-1,2-benzoisothiazolyl group, 2-oxo-1,2-dihydro-1-pyridinyl group, imidazolyl group, pyrazolyl group, 3,5-diethyl-1,2,4-triazol-1-yl group, 5- or 6-bromobenzotriazol-1-yl group, 5-methyl-1,2,3,4-triazol-1-yl group, benzimidazolyl group, 4-methoxyphenylazo group, 4-pivaloylaminophenylazo group, and 2-hydroxy-4-propanoylphenylazo group), a group connected by a sulfur atom (e.g., phenylthio group, 2-carboxyphenylthio group, 2-methoxy-5-t-octylphenylthio group, 4-methanesulfonylphenylthio group, 4-octanesulfonylamidophenylthio group, benzylthio group, 2-cyanoethylthio group, 1-ethoxycarbonyltridecylthio group, 5-phenyl-2,3,4,5-tetrazolylthio group, 2-benzothiazolyl group, thiocyano group, N,N-diethylthiocarbonylthio group, and dodecyloxythiocarbonylthio group), and a group connected by a carbon atom (e.g., triphenylmethyl group, hydroxymethyl group, N-morpholinomethyl group, and a group represented by the formula:

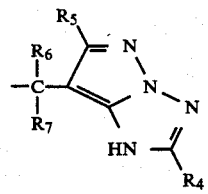

(where $R_6$ and $R_7$ each denote a hydrogen atom, alkyl group, aryl group, or heterocyclic group; and $R_4$ and $R_5$ are defined as above).

In the case where $R_4$, $R_5$, or X is a divalent group to form a bis modification, $R_4$ and $R_5$ each are substituted or unsubstituted alkylene group (e.g., methylene group, ethylene group, 1,10-decylene group, and —CH$_2$CH$_2$—O—CH$_2$CH$_2$—), substituted or unsubstituted phenylene group (e.g., 1,4-phenylene group, 1,3-phenylene group, and those groups represented by the following formulas

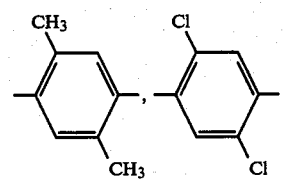

—NHCO—R$_8$—CONH— group where R$_8$ is a substituted or unsubstituted alkylene group or phenylene group such as those represented by the following formulas

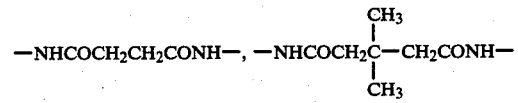

The following are examples of pyrazolo[1,5-b][1,2,4,]triazole derivative represented by the above formula (XI). Needless to say, this invention is not limited to them.

1
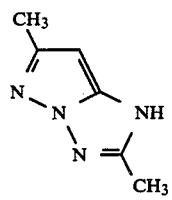
2
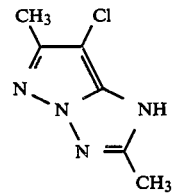
3
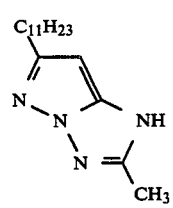
4
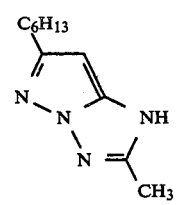
5
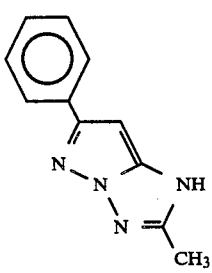
6
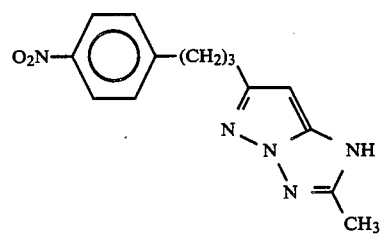
7
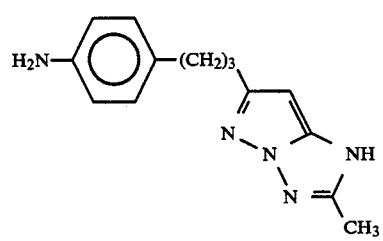
8
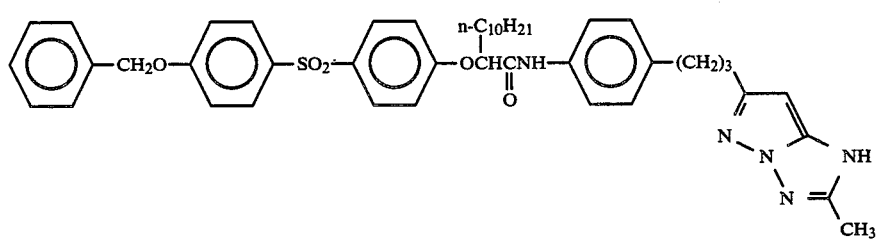
9
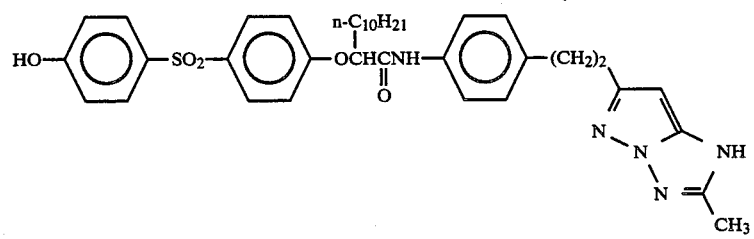
10
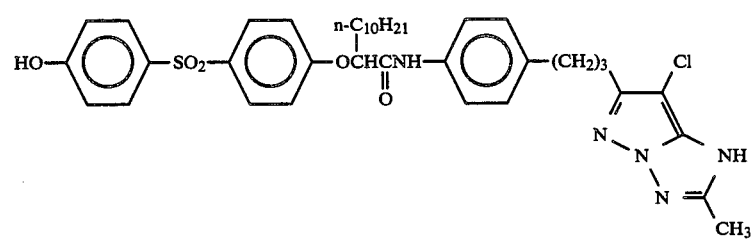

-continued
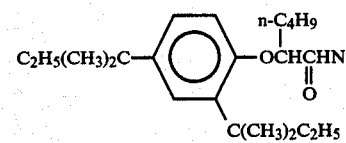 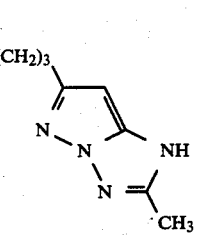
11
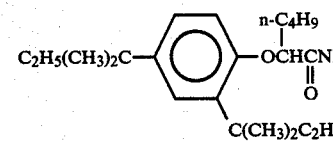 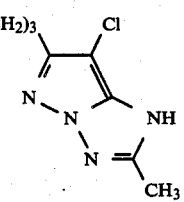
12
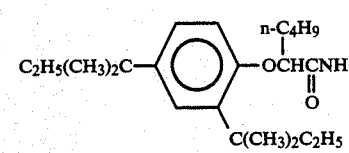 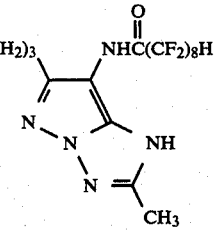
13
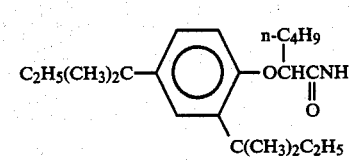 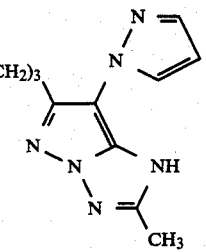
14
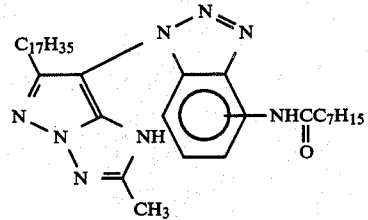
15
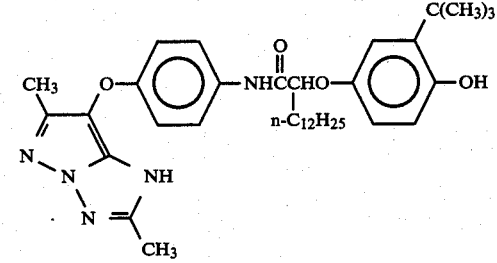
16
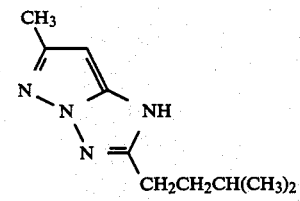
17
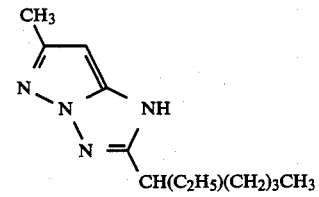
18

-continued
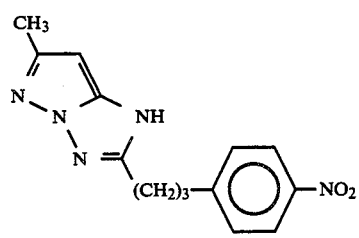 19
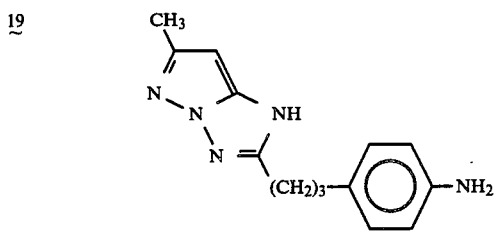 20
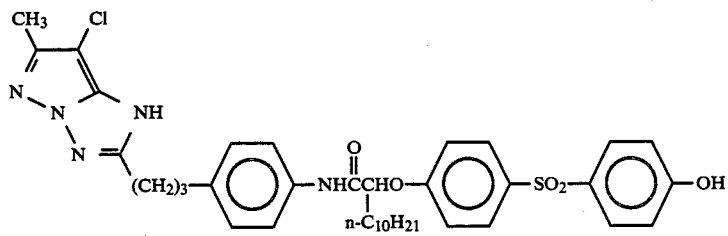 21
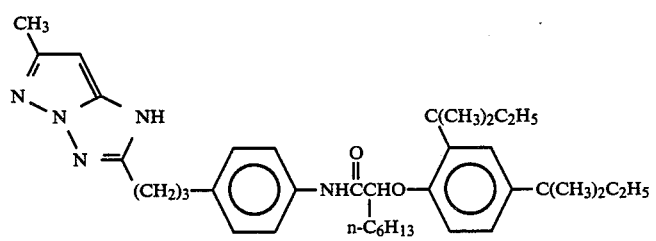 22
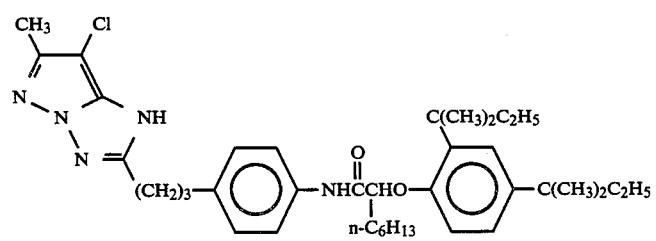 23
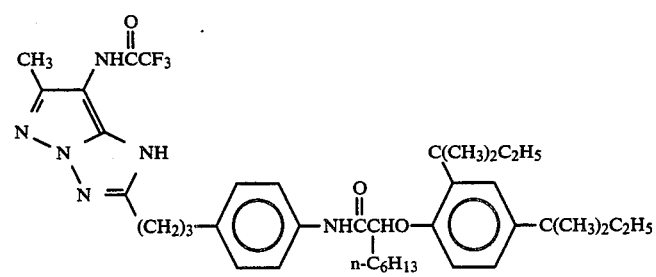 24
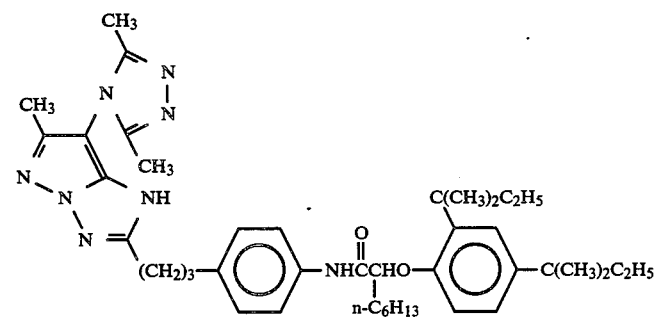 25

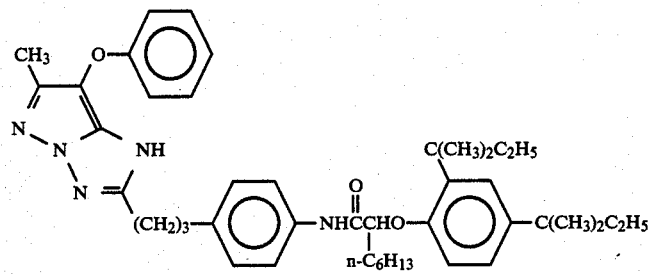
26
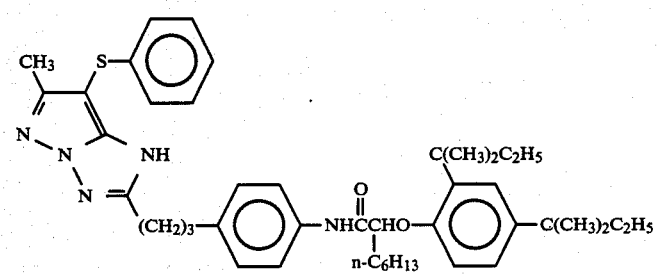
27
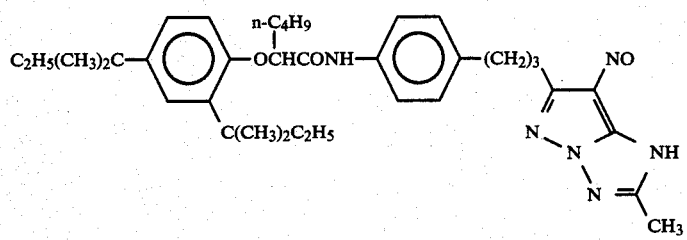
28
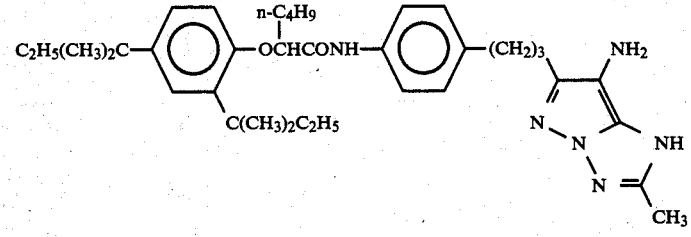
29
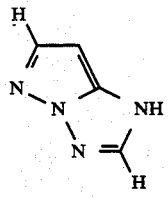
30
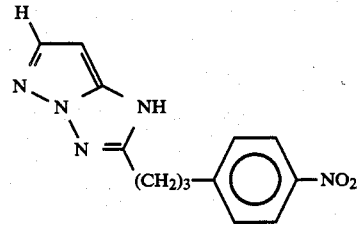
31
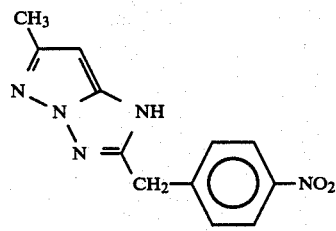
32
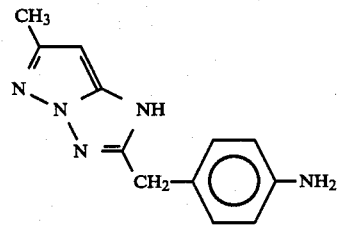
33

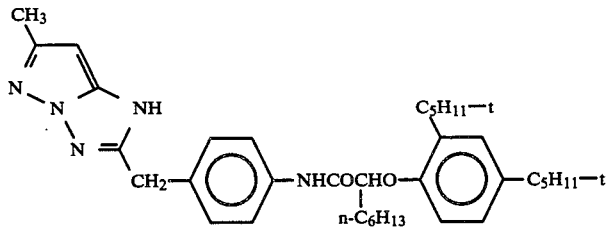

34

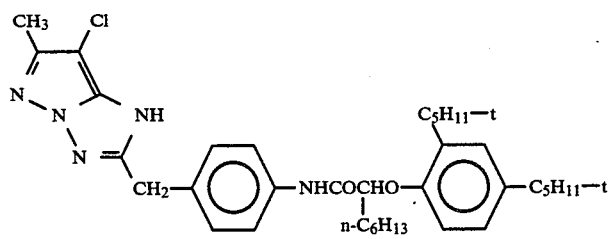

35

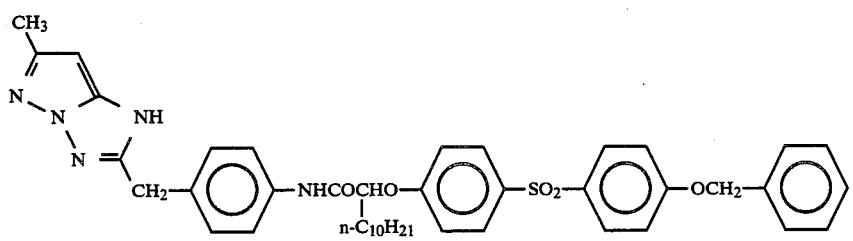

36

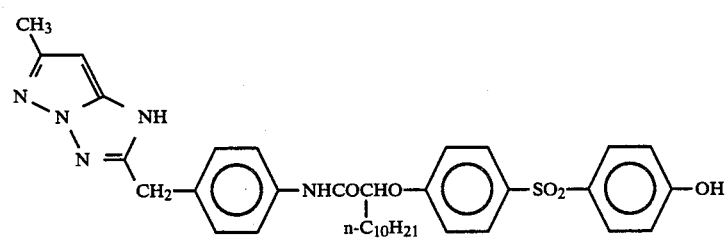

37

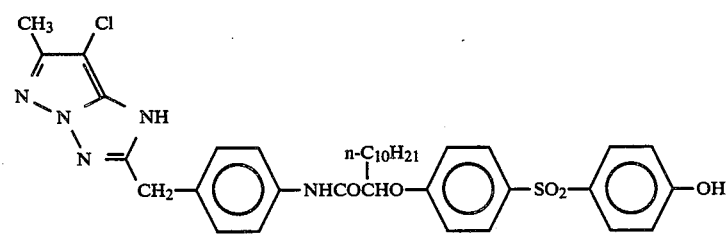

38

The following table shows the melting point of some of the compounds illustrated above.

| Compound No. | Melting point (°C.) | Compound No. | Melting point (°C.) |
|---|---|---|---|
| 1 | 274–275* | 28 | 95 |
| 2 | 250–255* | 30 | 200–205 |
| 3 | 154–155 | 31 | 165–170 |
| 4 | 105–110 | 32 | 251 |
| 5 | ca. 190* | 33 | 236° |
| 7 | 199–203 | 34 | 201–205 |
| 17 | 140–142 | 35 | 206–209 |
| 18 | 110–115 | 36 | 182–188 |
| 19 | 203–212 | 37 | 182–188 |
| 20 | ca. 180 | 38 | 175–180 |
| 25 | ca. 120 | | |

*decomposed

According to the process of this invention, new azapentalene compounds, pyrazolo[1,5-b][1,2,4]triazole derivatives can be prepared effectively. They can be used as a photographic magenta coupler as such. Moreover, they are useful as an intermediate for other magenta couplers, as dye developer for diffusion transfer process, and as an intermediate for photographic sensitizing dyes. They will also be used as a physiologically active substance and as an intermediate for pharmaceutical products.

The new azapentalene compound as a magenta coupler combines with an oxidation product of an aromatic primary amine to form a magenta dye which is superior in fastness to light and heat to a magenta dye formed by the conventional pyrazolone coupler.

The invention will be understood more readily by reference to the following examples; however, these examples are intended to illustrate the invention and are not to be construed to limit the scope of the invention.

EXAMPLE 1

(Synthesis of compound 1 illustrated above)

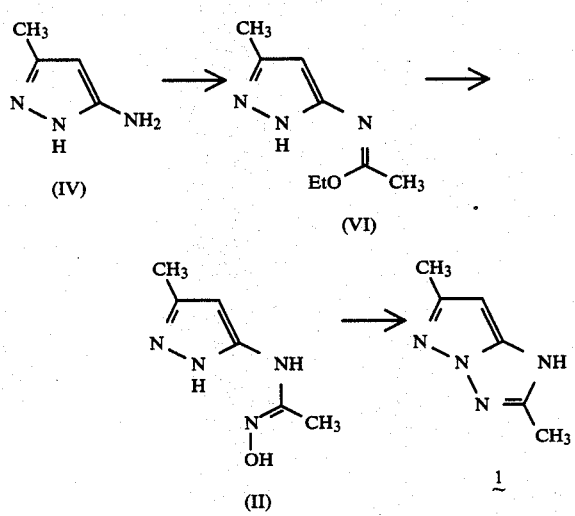

2.4 g (25 mmol) of 5-amino-3-methylpyrazole (IV), which is a reaction product of 3-aminocrotononitrile and hydrazine hydrate, and 6.0 g (37 mmol) of triethyl orthoacetate were heated in 20 ml of toluene under reflux for about 10 hours. Toluene was distilled away, and there was obtained an oily crude product of (VI).

NMR spectrum (CDCl$_3$): δ(ppm): 1.28 (3H, t, J=7.5), 1.96 (3H, s), 2.22 (3H, s), 4.19 (2H, q, J=7.5), 5.50 (1H, s).

2.6 g (37 mmol) of hydroxylamine hydrochloride was dissolved in 20 ml of methanol. To the solution kept at 0° C. was added 7.4 ml of 28% solution of sodium methoxide in methanol. After the separated sodium chloride had been filtered off, the reaction product was added to a methanol solution of (VI) at 0° C. The resulting solution was stirred at room temperature for about 1 hour. Methanol was distilled away and the resulting crystals were washed with chloroform. Thus there was obtained 3.2 g (83%) of (II). Melting point: 180°–185° C. (decomposed).

NMR spectrum (DMSO-d$_6$): δ(ppm): 1.87 (3H, s), 2.12 (3H, s), 5.65 (1H, s)

| Elemental analysis: | C (%) | H (%) | N (%) |
|---|---|---|---|
| Calculated | 46.74 | 6.54 | 36.34 |
| Found | 46.66 | 6.63 | 36.10 |

1.5 g (9.7 mmol) of (II) was dissolved in 150 ml of tetrahydrofuran (THF), and to the resulting solution was added 1.2 g of triethylamine and then 2.2 g of p-toluenesulfonyl chloride gradually at room temperature. After stirring for 30 minutes, 150 ml of THF was added and the solution was heated under reflux for 7 hours. The amine salt which had precipitated was filtered off, and the filtrate was concentrated. The resulting residues were purified by chromatography to yield 0.9 g (68%) of compound 1.

Melting point: 274°–275° C. (decomposed).
Mass spectrum: 136 (M+, 100%)

| Elemental analysis: | C (%) | H (%) | N (%) |
|---|---|---|---|
| Calculated | 52.93 | 5.92 | 41.15 |
| Found | 52.85 | 6.02 | 41.01 |

NMR spectrum (CDCl$_3$): pyridine—d$_5$=1:1)δ(ppm): 2.35 (3H, s), 2.43 (3H, s), 5.50 (1H, s).

There was also obtained as a by-product a small amount of compound 2 (melting point 250°–255° C., decomposed).

EXAMPLE 2

(Synthesis of compound 17 illustrated above)

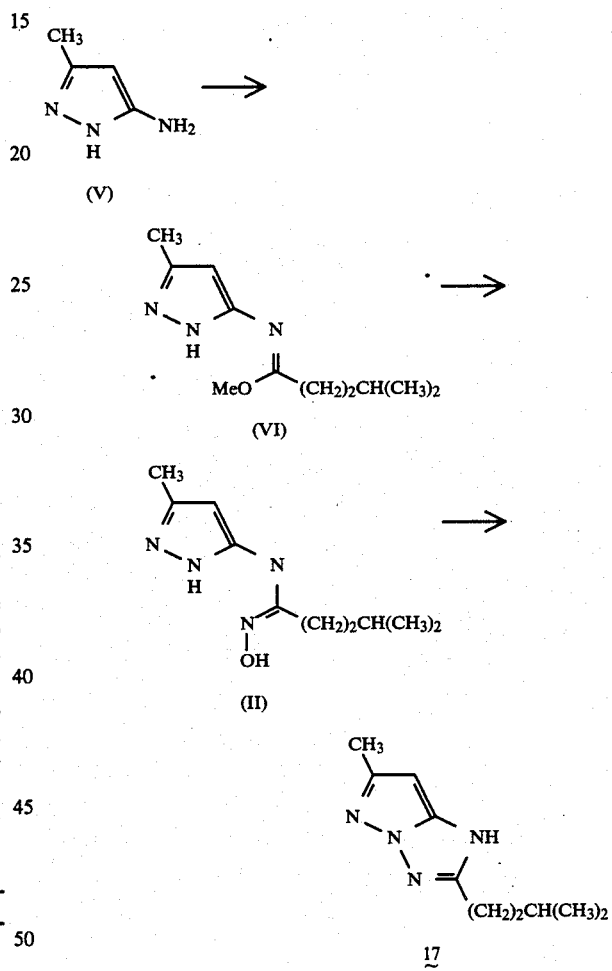

Trimethyl orthoisocaproate was synthesized in a 50% yield through imido ester hydrochloride from isocapronitrile. Boiling point: 75°–77° C./28 mmHg. 19.8 g (0.11 mmol) of this ortho-ester and 10.9 g (0.11 mol) of (IV) were heated in 200 ml of toluene under reflux for about 24 hours. Toluene wad distilled away under reduced pressure, and there was obtained an oily crude product of (VI). To this product kept at 0° C. was added a methanol solution of hydroxylamine prepared from 11.7 g (0.17 mol) of hydroxylamine hydrochloride and 34 ml of 28% sodium methoxide, followed by stirring at room temperature for 1 hour. Methanol was distilled away under reduced pressure. To the residues was added chloroform to precipitate powder crystals (12 g (52%)) of (II), which were subsequently filtered off. The crystals were dissolved in 3 liters of tetrahydrofuran. To the solution was added 6.9 g (68 mmol) of triethylamine and 13.1 g (68 mmol) of p-toluenesulfonyl chloride, followed by the same steps as in Example 1. Thus there was obtained 7.1 g (65%) of the compound 17. Melting point: 140°–142° C. Mass spectrum: 192 (M+) 136 (b. p)

NMR spectrum (CDCl$_3$): δ(ppm): 0.90 (6H, d, J=6), 1.55–1.90 (3H), 2.45 (3H, s), 2.90 (2H, brt, J=7), 5.60 (1H, s), 13.3 (1H).

EXAMPLE 3

(Synthesis of compound 19 illustrated above)

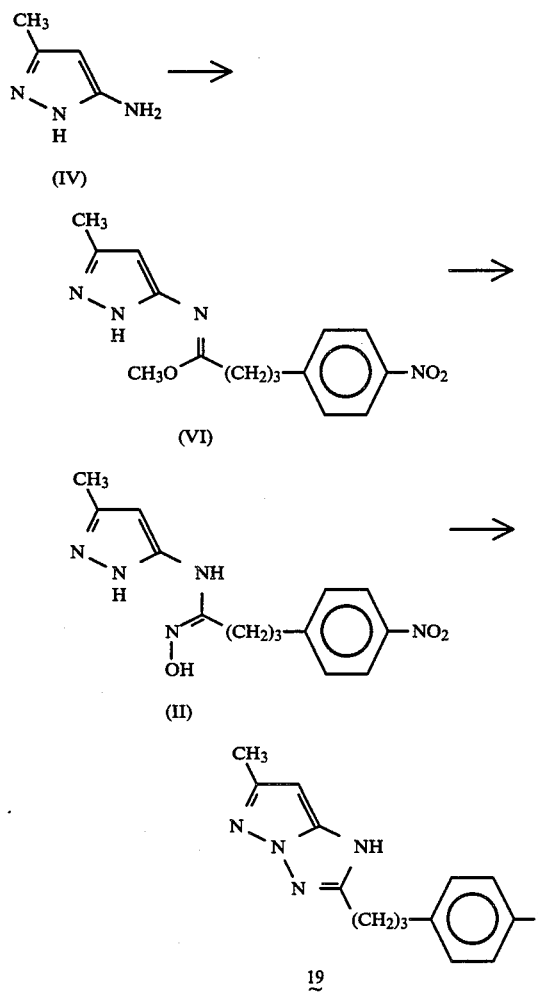

9.2 g (34 mmol) of trimethyl ortho-4-(p-nitrophenyl)-butyrate (prepared from 4-(p-nitrophenyl)butyric acid through a nitrile according to Pinner method) and 5 g (51 mmol) of 3-amino-5-methylpyrazole (IV) were heated in 100 ml of toluene under reflux for 20 hours. Toluene was distilled away under reduced pressure, and there was obtained a crude product of (VI). This product was dissolved in 100 ml of methanol. To the resulting solution kept at 0° C. was added a methanol solution of hydroxylamine prepared from 3.5 g (50 mmol) of hydroxylamine hydrochloride in the same way as in Example 1. The solution was stirred at room temperature for 1 hour. The solution was poured into 1 liter of water with stirring to form precipitates. The precipitates were filtered out and washed thoroughly with dichloromethane. Thus there was obtained (II) in the form of crystalline powder. Yield: 6.7 (65%).

Melting point: 165°–166° C.

2 g (6.6 mmol) of (II) was dissolved in 80 ml of tetrahydrofuran (THF), and to the solution was added 0.73 g (7.3 mmol) of triethylamine with stirring. To the solution was slowly added 1.4 g (7.3 mmol) of p-toluenesulfonyl chloride dissolved in 50 ml of THF, followed by stirring for 15 minutes. Precipitates of triethylamine hydrochloride were filtered off and washed with 10 ml of THF. The filtrate was refluxed for about 7 hours under a nitrogen stream. THF was distilled away under reduced pressure. The residues were dissolved in a small amount of methanol. To the solution was added 100 ml of water with stirring to form light brown precipitates. The precipitates were filtered with sucking. Upon recrystallization from a mixed solvent of acetonitrile and methanol, there was obtained 1.2 g (63%) of compound 19. Melting point: 203°–212° C.

Mass spectrum analysis: 285 (M+) 149 (b. p)

NMR spectrum (DMSO-d$_6$): δ(ppm): 2.05 (2H, m), 2.45 (3H, s), 2.56–2.86 (4H, m), 5.60 (1H, s), 7.25 (2H, d, J=80), 8.05 (2H, d, J=8.0).

EXAMPLE 4

(Synthesis of compounds 20, 22, and 25 illustrated above)

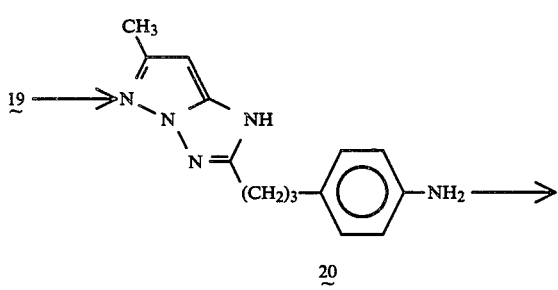

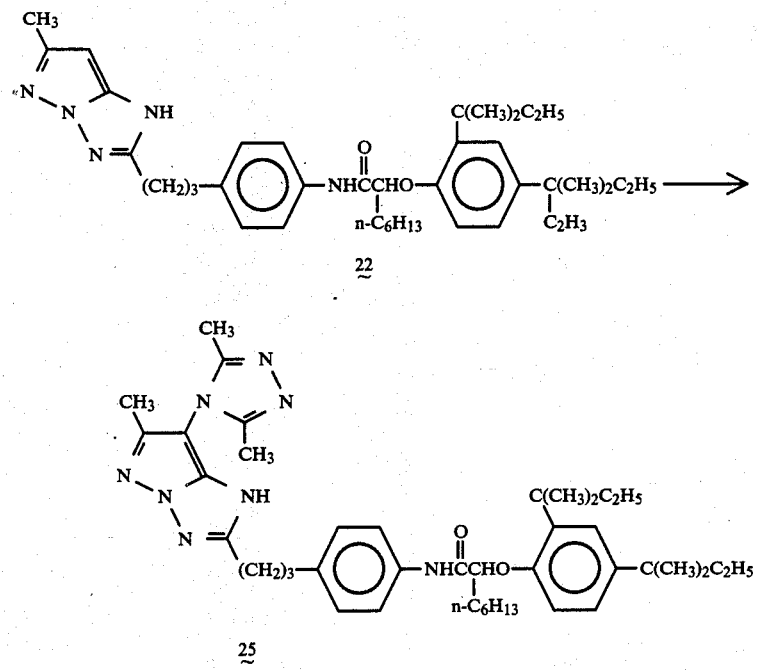

To 100 ml of isopropyl alcohol were added 20 g (0.36 mmol) of reduced iron, 1.4 g (2.8 mmol) of ammonium chloride, and 10 ml of water. The solution was heated with vigorous stirring to such an extent that reflux took place. 0.3 ml of conc. hydrochloric acid was added and the solution was refluxed for 30 minutes. To the solution was added over 20 minutes 15.2 g (53.2 mmol) of compound 19, followed by refluxing for 1 hour. The solution was filtered through sellaite, followed by washing with ethanol. After concentration, the filtrate was dissolved in 2N HCl aqueous solution, and the solution was washed with ethyl acetate. The water phase was neutralized with aqueous ammonia for precipitation. The precipitates were washed with water and then with acetonitrile, followed by drying. Thus there was obtained 10.9 g (80%) of compound 20 in the almost pure form.

Melting point: −180° C.

NMR spectrum (DMSO-d$_6$): δ(ppm): 1.90 (2H, br, quintet, J=−7), 2.46 (3H, s), 2.3–2.8 (4H), 5.60 (1H, s), 6.55 (2H, d, J=8.5), 6.93 (2H, d, J=8.5).

3.6 g (14.0 mmol) of compound 20 was dissolved in a mixed solvent composed of 30 ml of N,N-dimethylacetamide and 60 ml of acetonitrile. The solution was heated under reflux. To this solution was added over 20 minutes 20 ml of acetonitrile solution containing 6.1 g (15.4 mmol) of acid chloride [(t;13 C$_5$H$_{11}$)$_2$C$_6$H$_3$OCH(n—C$_6$H$_{13}$(COCl]. The solution was further heated under reflux for 30 minutes. After cooling, the solution was poured into 300 ml of water, followed by extraction with ethyl acetate. The ethyl acetate phase was washed with saturated aqueous solution of sodium chloride and dried on anhydrous magnesium sulfate, followed by concentration. After separation and purification by silica gel chromatography, there was obtained 7.0 g (81%) of compound 22

NMR spectrum (CDCl$_3$): δ(ppm): 0.50–1.00 (7H, m), 1.00–2.15 (30H, m), 2.45 (3H, s), 2.46–2.80 (4H, m), 4.68 (1H, t, J=6.5), 5.60 (1H, s), 6.88–7.33 (6H, m), 7.66 (1H, d, J=9.0), 7.88 (1H, br, s).

3.1 g (5.00 mmol) of compound 22 was added to 25 ml of acetic acid, followed by stirring at room temperature. To the solution was added 586 mg (5.00 mmol) of isoamyl nitrite, followed by stirring for 1 hour. The resulting solution was slowly added to 300 ml of water for precipitation. The precipitates were filtered off and washed with water, followed by drying under reduced pressure. Thus there was obtained 2.9 g (91%) of a solid 7-nitroso compound.

Melting point: Ca. 90° C.

2.9 g (4.5 mmol) of the 7-nitroso compound was dissolved in 50 ml of ethanol, and the solution was refluxed under a nitrogen stream. 4.27 g (22.5 mmol) of stannous chloride dissolved in 10 ml of conc. hydrochloric acid was added dropwise over 10 minutes. After further refluxing for 30 minutes and cooling, the solution was poured into 150 ml of water, followed by extraction with ethyl acetate. The ethyl acetate phase was dried with anhydrous magnesium sulfate, followed by concentration to dryness. Thus there was obtained a complex composed of the 7-amino compound and tin. It was used for the subsequent reaction without being changed into a free amino compound.

To this 7-amino compound were added 100 ml of toluene and 0.49 g (5.0 mmol) of 2,5-dimethyl-1,3,4-oxadiazole, followed by refluxing for about 5 hours. The resulting product was poured into 250 ml of water, followed by extraction with ethyl acetate. The ethyl acetate phase was dried on anhydrous magnesium sulfate, followed by concentration. After separation and purification by silica gel chromatography, there was obtained 2.2 g (70%) of solid compound 25.

Melting point: −120° C.

NMR spectrum (CDCl$_3$): δ(ppm): 0.48–1.00 (7H, m), 1.05–2.20 (30H, m), 2.43 (3H, s), 2.46 (6H, s), 2.46–2.80 (4H, m), 4.67 (1H, t, J=6.5), 6.60 (1H, d, J=8.5), 6.90–7.35 (6H, m), 7.85 (1H, s).

EXAMPLE 5

(Synthesis of compound 30)

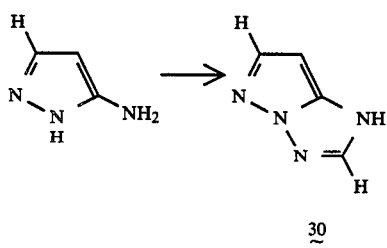

8.3 g (0.1 mol) of commercially available 3-aminopyrazole and 22.2 g (0.15 mol) of triethyl orthoformate were dissolved in 100 ml of toluene, followed by refluxing for about 10 hours. Toluene was distilled away under reduced pressure. The residues were dissolved in 50 ml of methanol. To the solution kept at 0° C. was added a methanol solution containing hydroxylamine prepared from 10.4 g (0.15 mol) of hydroxylamine hydrochloride in the same way as in Example 2. The solution was stirred at room temperature for 1 hour. Methanol was distilled away under reduced pressure at as low a temperature as possible. Upon addition of dichloromethane to the residues, there was obtained compound (II) ($R_1=R_2=H$) in the form of crystals. Yield: 8.2 g (65%).

5 g (40 mmol) of this amidoxime was reacted with p-toluenesulfonyl chloride and triethylamine in THF in the same manner as in Example 1. The solution was heated under reflux. Upon purification by silica gel chromatography, there was obtained 2.6 g (60%) of compound 30. Melting point 200°–205° C.

NMR spectrum (DMSO-$d_6$): δ(ppm): 5.75 (1H, d, J=2.5), 7.53 (1H, d, J=2.5), 8.05 (1H, s).

EXAMPLE 6

(Synthesis of compound 31)

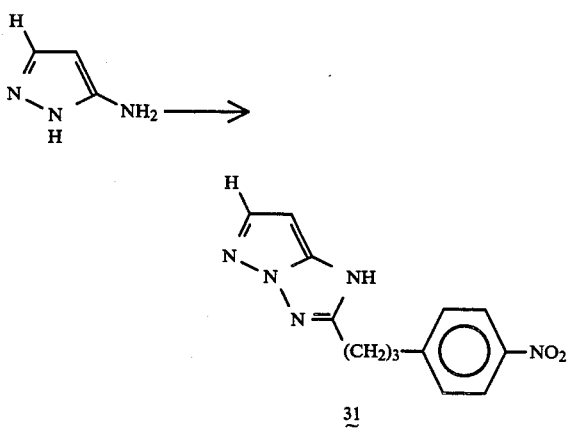

There was obtained 19 g (69%) of (II) ($R_2=H$, $R_1=-(CH_2)_3C_6H_4NO_2$) from 8.3 g (0.1 mol) of 3-aminopyrazole and 27.1 g (0.1 mol) of trimethyl ortho-4-(p-nitrophenyl)-butyrate in almost the same way as in Example 1. 5 g (18 mmol) of this amidoxime gave 3.1 g (68%) of compound 31.

Melting point: 165°–170° C.

NMR spectrum (DMSO-$d_6$): δ(ppm): 2.04 (2H, m), 2.55–2.86 (4H, m), 5.78 (1H, d, J=2.5), 7.25 (2H, d, J=8.0), 7.54 (1H, d, J=2.5), 8.05 (2H, d, J=8.0).

EXAMPLE 7

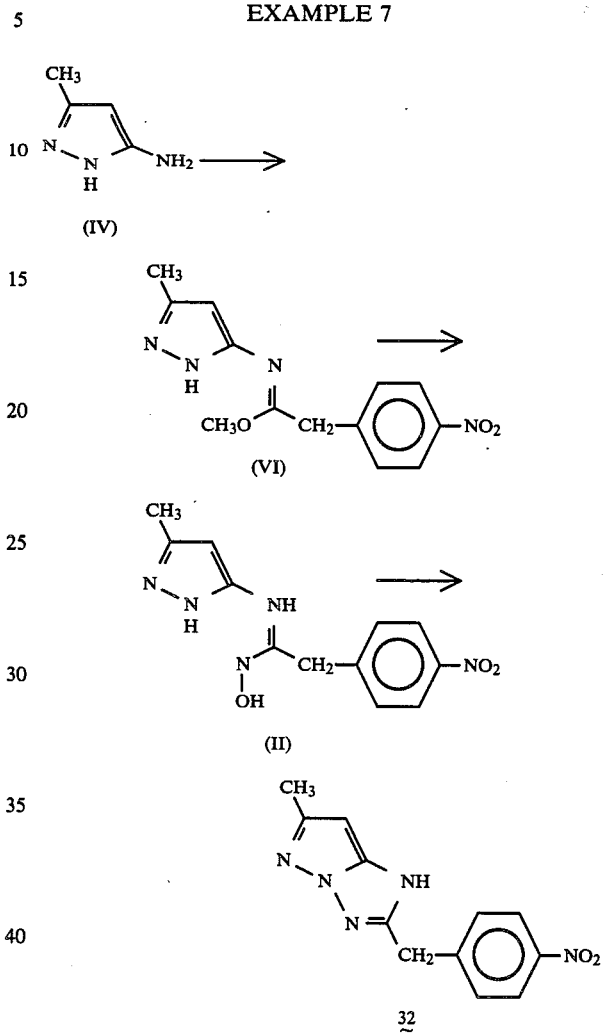

p-Nitrophenylketene dimethylacetal was synthesized in the following manner. At first, 100 g (0.617 mol) of p-nitrobenzenzylcyanide was vigorously stirred in a mixed solvent composed of 19.8 g (0.617 mol) of methanol and 75 ml of dioxane, and dry hydrogen chloride gas was introduced into it over about 1.5 hours. When the quantity of the gas absorbed exceeded 22.5 g, the introduction of the gas was suspended and the reaction product was cooled overnight in a refrigerator. After crushing, the precipitates were added to ether, filtered off, washed thoroughly with ether, and finally dried in a vacuum desiccator. Thus there was obtained 138 g (79%) of imide ester hydrochloride. To this compound was added 211 ml of methanol, followed by stirring for a while for complete dissolution. After addition of 400 ml of ether, the solution was heated under reflux for about 15 hours. After cooling to room temperature, about 300 ml of 10% $Na_2CO_3$ solution was added slowly, and then 1 liter of ethyl acetate was added for extraction. The ethyl acetate phase was washed with 10% $Na_2CO_3$ solution and then dried on anhydrous $K_2CO_3$, followed by filtration. The solvent was distilled away under reduced pressure to cause crystals to separate out. The crystals were washed thoroughly with ether to give 36 g (49%) of almost pure p-nitrophenylketene dimethylacetal.

12.0 g (0.124 mol) of aminopyrazole (IV) and 26.0 g (0.124 mol) of p-nitrophenylketene dimethylacetal were dissolved in 200 ml of toluene. To the solution was added 0.04 ml (0.5 mol%) of methanesulfonic acid, followed by heating under reflux for about 4 hours. Toluene was distilled away under reduced pressure, and the residues were dissolved in 200 ml of methanol. To the solution being cooled in an ice bath was added in two portions a methanol solution of hydroxylamine prepared from 51.8 g (0.744 mol) of hydroxylamine hydrochloride and 150 ml of 28% sodium methoxide solution in methanol. The solution was stirred at room temperature for about 2 hours, and allowed to stand overnight. Methanol was distilled away under reduced pressure (at a temperature below 50° C.) until the volume was reduced to about one half. The solution was poured into 1 liter of water for precipitation. The precipitates were filtered off and dried. There was obtained 22.9 g (67%) of (II).

There was obtained 2.7 g (58%) of compound 32 from 5.0 g of (II) in the same way as in Example 3.

Melting point: −251° C. (decomposed).

EXAMPLE 8

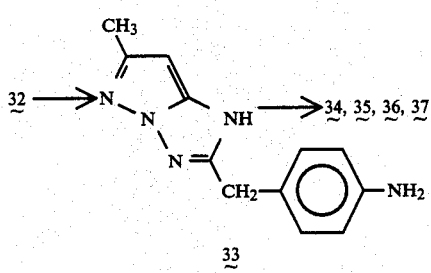

To 20 ml of water were added 17 g of reduced iron, 1.1 g of ammonium chloride, and 1.2 ml of acetic acid. The solution was heated under reflux for about 20 minutes under a nitrogen stream. To the solution was further added 100 ml of isopropyl alcohol, followed by refluxing. To the solution was added dropwise over 15 minutes 11.0 g (42.8 mmol) of compound 32. About 30 minutes later, compound 32 was not detected by thin-layer chromatography. 100 ml of DMF was added, followed by stirring for 5 minutes. Without being cooled, the reaction liquid was filtered through Celite, followed by washing with 50 ml of DMF and then 200 ml of ethanol. The filtrate was evaporated under reduced pressure, and the resulting crystals were suspended in acetonitrile. The suspension was filtered, followed by washing with acetonitrile. Thus there was obtained 9.8 g (101%) of compound 23 containing a small amount of iron.

Melting point: 236° C. (decomposed).

3.5 g (15.4 mmol) of compound 33 was dissolved in a mixed solvent composed of 50 ml of acetonitrile and 25 ml of dimethylacetamide (DMAC), followed by heating under reflux. To the solution was added dropwise over 10 minutes 6.09 g (15.4 mmol) of

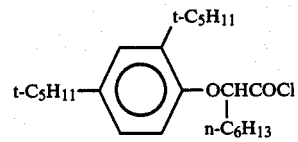

dissolved in 10 ml of acetonitrile, followed by heating under reflux for 1 hour. The reaction liquid was poured into 500 ml of iced water, followed by neutralization and extraction with ethyl acetate. The ethyl acetate layer was dried on anhydrous magnesium sulfate, followed by filtration and distillation under reduced pressure. The residues were recrystallized from acetonitrile. Thus there was obtained 5.36 g (59%) of compound 34.

Melting point: 201°–205° C.

5.32 g (9.08 mmol) of compound 34 was dissolved in a mixed solvent of THF (50 ml) and dichloromethane (100 ml), with stirring. To the resulting solution was added 1.15 g (8.63 mmol) of N-chlorosuccinimide, with stirring for 15 minutes. The reaction liquid was washed with water in a separating funnel. The organic phase was dried with magnesium sulfate, followed by filtration and concentration under reduced pressure. The crystals thus obtained were dissolved in ethanol and the ethanol solution was treated with activated carbon. Upon recrystallization from a 4:1 mixed solvent of acetonitrile and ethyl acetate, there was obtained 2.99 g (53%) of compound 35. Melting point: 206°–209° C.

2.50 g (11.0 mmol) of compound 33 was dissolved in a mixed solvent of acetonitrile (40 ml) and DMAC (20 ml). To the solution under reflux was added over 30 minutes a solution prepared by dissolving 6.74 g (12.1 mmol) of a compound of the formula below:

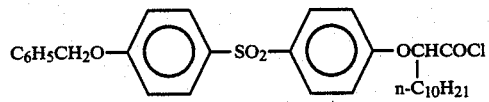

in 25 ml of acetonitrile. The solution was heated under reflux for 1 hour. The reaction liquid was poured into 500 ml of water, followed by extraction with ethyl acetate. The ethyl acetate phase was dried and then concentrated under reduced pressure. Upon addition of acetonitrile, there was obtained 5.58 g (68%) of compound 36. Melting point: 204°–214° C.

5.25 g (7.02 mmol) of compound 36 was dissolved in 70 ml of THF, and 0.5 g of 10% Pd/C was added to the solution. The solution was heated with stirring at 70° C. for 15 hours in an autoclave under a 50 atm hydrogen atmosphere. After cooling, the catalyst was filtered off and THF was distilled away. Upon recrystallization from a 4:1 mixed solvent of ethyl acetate and hexane, there was obtained 3.86 g (84%) of compound 37. Melting point: 182°–188° C.

3.65 g (5.55 mmol) of compound 37 was chlorinated with 726 mg (5.44 mmol) of N-chlorosuccinimide in the same way as used for synthesis of compound 35. Upon recrystallization from a mixture of ethyl acetate and n-hexane, there was obtained 2.44 g (64%) of compound 38. Melting point: 175°–180° C.

Having described a specific embodiment of our bearing, it is believed that modification and variation of our invention is possible in light of the above teachings.

What is claimed is:

1. A process for producing pyrazolo[1,5-b][1,2,4]triazole derivatives which comprise subjecting a compound represented by the formula:

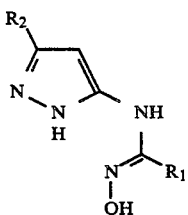

(where $R_1$ and $R_2$ independently represent a hydrogen atom or a substituted or unsubstituted alkyl group, or a substituted or unsubstituted aryl group) to dehydrating ring closure to give a compound represented by the formula:

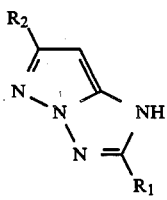

(where $R_1$ and $R_2$ are defined as above).

2. The process for producing pyrazolo[1,5-b][1,2,4]triazole derivatives as claimed in claim 1 wherein the ring closure is conducted by using a dehydrating agent in the presence of a base.

3. The process for producing pyrazolo[1,5-b][1,2,4]triazole derivatives as claimed in claim 2 wherein the ring closure is conducted at 40° to 100° C. for 2 to 10 hours in an inert solvent.

4. The process for producing pyrazolo[1,5-b][1,2,4]triazole derivatives as claimed in claim 1 wherein the ring closure is conducted at 40° to 100° C. for 2 to 10 hours in an inert solvent.

5. The process for producing pyrazolo[1,5-b][1,2,4]triazole derivatives as claimed in claim 1 wherein the compound represented by the formula below

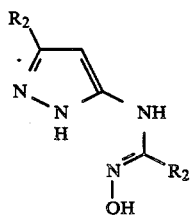

(where $R_1$ and $R_2$ independently represent a hydrogen atom or a substituted or unsubstituted alkyl group, or a substituted or unsubstituted aryl group) is prepared by reacting a compound represented by the formula below

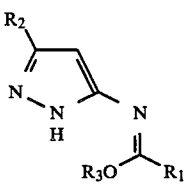

(where $R_1$ and $R_2$ are defined as above, and $R_3$ is an alkyl group) with hydroxylamine.

6. The process for producing pyrazolo[1,5-b][1,2,4]triazole derivatives as claimed in claim 5 wherein the compound represented by the formula below

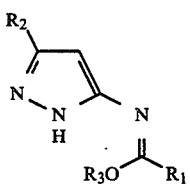

(where $R_1$ and $R_2$ independently represent a hydrogen atom or a substituted or unsubstituted alkyl group, or a substituted or unsubstituted aryl group; and $R_3$ is an alkyl group) is prepared by reacting aminopyrazole represented by the formula below

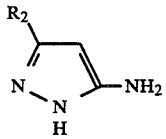

(where $R_2$ is defined as above) with an ortho-ester represented by the formula below

(where $R_1$ and $R_3$ are defined as above) or a ketene acetal represented by the formula below

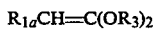

(where $R_{1a}$ is a group which, in combination with $CH_2-$, forms the above-mentioned $R_1$ group which is a substituted or unsubstituted alkyl group, and $R_3$ is defined as above).

7. The process for producing pyrazolo[1,5-b]-[1,2,4]triazole derivatives as claimed in claim 1, wherein the unsubstituted alkyl group has 1 to 22 carbon atoms.

8. The process for producing pyrazolo[1,5-b]-[1,2,4]triazole derivatives as claimed in claim 1, wherein the aryl group is a phenyl group or a naphthyl group.

9. The process for producing pyrazolo[1,5-b]-[1,2,4]triazole derivatives as claimed in claim 1, wherein the substituted alkyl group is selected from the group consisting of halogen-substituted alkyl groups, alkoxy-substituted alkyl groups, acylamido-substituted alkyl groups, sulfonamido-substituted alkyl groups and alkyl groups substituted by a substituted or unsubstituted aryl group.

10. The process for producing pyrazolo[1,5-b]-[1,2,4]triazole derivatives as claimed in claim 1, wherein the substituted aryl group is selected from the group consisting of a halogenophenyl group, a nitrophenyl group, a cyanophenyl group and an alkoxylphenyl group.

11. The process for producing pyrazolo[1,5-b]-[1,2,4]triazole derivatives as claimed in claim 6, wherein the process is conducted at 40° to 150° C. for 10 minutes to 20 hours.

12. The process for producing pyrazolo[1,5-b]-[1,2,4]triazole derivatives as claimed in claim 6, wherein the molar ratio of aminopyrazole to orthoester is in the range of 2:1 to 1:2.

13. The process for producing pyrazolo[1,5-b]-[1,2,4]triazole derivatives as claimed in claim 3 wherein the dehydrating agent is selected from the group consisting of p-toluenesulfonyl chloride, methane-sulfonyl chloride, trifluoromethane-sulfonyl chloride, phosphorous oxychloride and thionyl chloride or the base is a tertiary amine.

14. The process for producing pyrazolo[1,5-b]-[1,2,4]triazole derivatives as claim 2, wherein the amount of base is 0.5 to 2 equivalent.

* * * * *